(12) United States Patent
van Dongen et al.

(10) Patent No.: US 10,942,171 B2
(45) Date of Patent: *Mar. 9, 2021

(54) METHODS, REAGENTS AND KITS FOR FLOW CYTOMETRIC IMMUNOPHENOTYPING

(71) Applicant: Erasmus University Medical Center Rotterdam, Rotterdam (NL)

(72) Inventors: Jacobus Johannes Maria van Dongen, Rotterdam (NL); Jose Alberto Orfao de Matos Correia e Vale, Salamanca (ES); Juan Alejandro Flores-Montero, Salamanca (ES); Julia Maria Almeida Parra, Salamanca (ES); Vincent Henricus Johannes van der Velden, Capelle aan den IJssel (NL); Sebastian Böttcher, Stampe (DE); Andrew Craig Rawstron, Yorkshire (GB); Ruth Mary de Tute, West Yorkshire (GB); Ludovic Bernard Simon Lhermitte, Paris (FR); Vahid Asnafi, Bezons (FR); Ester Mejstrikova, Prague (CZ); Tomasz Szczepanski, Zabrze (PL); Paulo Jorge Monteiro Da Silva Lucio, Carnaxide (PT); Marta Martín Ayuso, Salamanca (ES); Carlos Eduardo Pedreira, Rio de Janeiro (BR)

(73) Assignee: Erasmus University Medical Center Rotterdam, Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/849,196

(22) Filed: Dec. 20, 2017

(65) Prior Publication Data

US 2018/0120301 A1    May 3, 2018

Related U.S. Application Data

(63) Continuation of application No. 13/376,103, filed as application No. PCT/NL2010/050332 on Jun. 2, 2010, now Pat. No. 9,880,158.

(30) Foreign Application Priority Data

Jun. 3, 2009    (EP) .................................... 09161870

(51) Int. Cl.
| | | |
|---|---|---|
| *G01N 33/533* | (2006.01) | |
| *G01N 15/14* | (2006.01) | |
| *G01N 33/50* | (2006.01) | |
| *G01N 33/532* | (2006.01) | |

(52) U.S. Cl.
CPC ......... *G01N 33/5094* (2013.01); *G01N 15/14* (2013.01); *G01N 33/5005* (2013.01); *G01N 33/5091* (2013.01); *G01N 33/532* (2013.01); *G01N 33/533* (2013.01); *G01N 2015/1402* (2013.01); *G01N 2015/1413* (2013.01)

(58) Field of Classification Search
CPC .......... G01N 33/5094; G01N 33/5005; G01N 33/5091; G01N 33/532; G01N 33/533; G01N 15/14
See application file for complete search history.

(56) References Cited

U.S. PATENT DOCUMENTS

| | | |
|---|---|---|
| 5,538,855 A | 7/1996 | Orfao de Matos Correira E Vale |
| 9,880,158 B2* | 1/2018 | Van Dongen ...... G01N 33/5094 |
| 10,209,245 B2* | 2/2019 | van Dongen ...... G01N 33/5094 |
| 2018/0180597 A1 | 6/2018 | Johannes et al. |
| 2018/0180598 A1 | 6/2018 | Johannes et al. |

OTHER PUBLICATIONS

Gorczyca et al. Subset of T-cell prolymphocytic leukemia expresses CD117. Potential target for therapy. Blood 104 (11): Part 2, pp. 218B (Nov. 16, 2004)) (Abstract).*

Nieto et al. Increased frequency (12%) of circulating chronic lymphocytic leukemia-like B-cell clones in healthy subjects using a highly sensitive multicolor flow cytometry approach. Blood 144 (1): 33-37 (Prepublished on-line May 6, 2009).*

Braylan et al. Optimal number of reagents required to evaluate hematolymphoid neoplasias: results of an international consensus meeting. Cytometry, 46 (1): 23-27 (Feb. 15, 2001).*

Rawstron et al. Flow cytometric protein expression profiling as a systematic approach for developing disease-specific assays: identification of a chronic lymphocytic leukaemia-specific assay for use in rituximab-containing regimen. Leukemia 20: 2102-2110 (2006).*

U.S. Appl. No. 15/848,223, filed Dec. 2017, van Dongen.*

Berrebi et al. The Significance of Elevated Beta 2-Microglobulin (b2-m) in BCLL: Evidence of in Vitro b2-m Secretion Following Activation of B-CLL Cells. Blood 114:4380 (2009).*

Drach et al., "Flow cytometric detection of cytoplasmic antigens in acute leukemias; implications for lineage assingment," Leukemia Research, New York, 17(5):455-461 (1993).

Haferlach et al., "Modern diagnostics in acute leukemias," Critical Reviews in Oncology/Hematology, Elsevier, Amsterdam, 56(2):223-234 (2005).

Braylan et al., "Optimal number of reagents required to evaluated hematolymphoid neoplasias: results of an international consensus meeting," Cytometry 46 (1):23-27, Feb. 15, 2001.

Kraan et al., Current Protocols in Cytometry 6.25.1-6.25.16, Jul. 2008.

(Continued)

*Primary Examiner* — Gailene Gabel

(74) *Attorney, Agent, or Firm* — Fish & Richardson P.C.

(57) ABSTRACT

The invention relates to the field of flow cytometry and more particularly to a panel of antibody reagents conjugated to fluorescent compounds. Provided are reagent compositions, comprising at least eight distinct fluorochrome-conjugated antibodies comprising a set of at least there identification antibodies for the identification of a leukocyte population of interest and at least four characterization antibodies for further characterization and/or classification of said leukocyte population. Also provided are kits and methods related to the reagent compositions.

10 Claims, 1 Drawing Sheet

(56) References Cited

OTHER PUBLICATIONS

Figure 1:
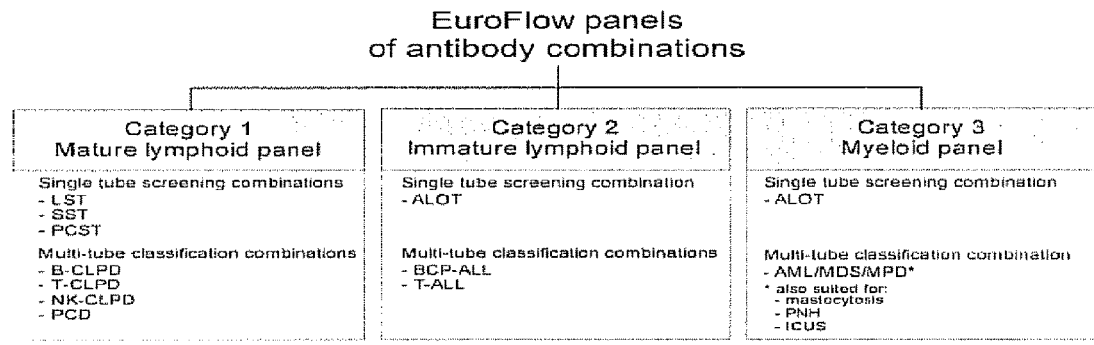

Nieto et al., Blood 144(1):33-37; published online May 6, 2009.
Rawston et al., Leukemia 20:2102-2110, 2006.
Brunetti et al., Br. J. Haematol. 145(5):665-7, Jun. 2009.
Martins et al., Transplant Proc. 41(3):943-6, Apr. 2009.
BD Biosciences. BD PAC-H7 Conjugated Antibody Reagents, 2008.
Abrams et al., "3-Carboxy-6-chloro-7-hydroxycoumarin: a highly fluorescent, water-soluble violet-excitable dye for cell analysis," Analytical Biochemistry 386(2):262-269, Mar. 15, 2009.
Anonymous, "Consensual European Immunophenotyping Panels for Leukemia," 6th PCRDT, http://infordoc.inserm.fr/serveur/egil.nsf/397fe8563d75f39bc12563f60028ec43/abd2433c0003368fc1256fec004cd30a?OpenDocument, retrieved from the internet Nov. 18, 2009, 14 pages.
Berhanu et al., "Optimized lymphocyte isolation methods for analysis of chemokine receptor expression," Journal of Immunological Methods 279(1-2):199-207, Aug. 1, 2003.
Boettcher et al., "Improved differntial diagnosis between who-defined mature B-cell malignancies using intergrated 8-color flow cytometry and novel software for multivariate analysis of immunophenotypic data," Haematologica—The Hemotology Journal 94(2):276, Jun. 2009.
Boulassel et al., "Immunophenotypic patterns of CD8+ T cell subsets expressing CD8alphaalapha and IL-7Ralpha in HIV-1-infected subjects," Clinical Immunology 124(2):149-157, Jul. 18, 2007.
Campana et al., "Immunophenotyping of leukemia," Journal of Immunological Methods 243(1-2):59-75, Sep. 21, 2000.
Lhermitte et al., "A single 8-color flow-cytometric immunostaining allows delineation of both typical myeloid and lymphoid acute leukemia and undifferenciated/immature acute leukemia (on behalf of the Euroflow Consortium," Haematologica—The Hematology Journal 94 (Suppl. 2):110-111 Jun. 2009, and 14th Annual Meeting of the Eurpoean-Hematology-Association; Berlin, Germany, Jun. 4-7, 2009.
Lhermitte et al., "A single 8-color flow-cytometric immunostaining allows delineation of both typical myeloid and lymphoid acute leukemia and undifferncieated/immature acute leukemia," Jun. 4, 2009, retrieved from the internet: http://www.euroflow.org/imagenes/publications/lhermitte,_alot_poster,_eha_2009,_berlin.pdf, retrieved Nov. 17, 2009.
Rawstron et al., "Selection of Markers for Identification of Disease-Specific Phenotypes for Diagnosis and Monitoring of B-Lymphoproliferative Disorders by Flow Cytometry," Haematologica—The Hematology Journal 94 (Suppl. 2):275-276, Jun. 2009.
Vaickus et al., "Immune Markers in Hematologic Malignancies," Critical Reviews in Oncology/Hematology 11(4):267-297, Dec. 1, 1991.
Van Dongen et al., "EuroFlow antibody panels for standardized n-dimensional flow cytometric immunophenotyping of normal, reactive and malignant leukocytes," Jun. 4, 2009, retrieved from the internet: http://www.euroflow.org/imagenes/news/euroflow_handout_on_antibody_panels.pdf, retrieved Nov. 17, 2009.
International Search Report from corresponding PCT Application No. PCT/NL2010/050332, dated Oct. 14, 2010, 8 pages.
Notification Concerning Transmittal of International Preliminary report on Patentability and Written Opinion from corresponding PCT Application No. PCT/NL2010/050332, dated Dec. 15, 2011, 24 pages.
Kappelmeyer et al., "Flow cytometric detection of intracellular myeloperoxidase, CD3 and 79a Interaction between monoclonal antibody clones, fluorochromes and sample preparation protocols," Journal of Immunological Methods 242:53-65, 2000.
Lhermitte et al., "Automated database-guided expert-supervised orientation for immunophenotypic diagnosis and classification of acute leukemia," Leukemia 32(4):874-881, Apr. 2018.
Van Dongen er al., "EuroFlow antibody panels for standardized n-dimensional flow cytometric immunophenotyping of normal, reactive and malignant leukocytes," Leukemia 26(9):1908-75, Sep. 2012, 212 pages.

\* cited by examiner

METHODS, REAGENTS AND KITS FOR FLOW CYTOMETRIC IMMUNOPHENOTYPING

CROSS-REFERENCE TO RELATED APPLICATIONS

This application is a continuation of U.S. patent application Ser. No. 13/376,103, filed Dec. 2, 2011 (issued as U.S. Pat. No. 9,880,158), which is a U.S. National Phase Application under 35 U.S.C. § 371 of International Patent Application No. PCT/NL2010/050332, filed on Jun. 2, 2010, which claims the benefit of EP 09161870.2, filed on Jun. 3, 2009, the entire contents of each of which is hereby incorporated by reference. U.S. patent application Ser. No. 15/849,233, filed Dec. 20, 2017 (pending) and U.S. patent application Ser. No. 15/848,719, filed Dec. 20, 2017 (issued as U.S. Pat. No. 10,209,245) are also continuation applications of U.S. patent application Ser. No. 13/376,103, filed Dec. 2, 2011 (issued as U.S. Pat. No. 9,880,158) and also claim priority to both International Patent Application No. PCT/NL2010/050332, filed on Jun. 2, 2010, and EP 09161870.2, filed on Jun. 3, 2009.

The invention relates to the field of flow cytometry and more particularly to a panel of antibody reagents conjugated to fluorescent compounds. They find their use in the immunophenotypic characterization of normal, reactive, regenerating and neoplastic cells in peripheral blood (PB), bone marrow (BM), pleural effusions, ascitis, cerebrospinal fluid (CSF), vitreous humor, synovial fluid, bronchoalveolar lavage, urine, spleen, liver, lymph node, and other tissue samples. Flow cytometric immunophenotyping of normal, reactive, regenerating, and malignant cells (in particular leukocytes) is currently being used for many applications in medicine, including immunology, hematology and oncology. Among others, said applications include monitoring of the immune system; diagnosis and classification of primary immunodeficiencies; immunophenotyping of leukemias, lymphomas and plasma cell dyscrasias; monitoring of low frequencies of malignant leukocytes as measure for treatment effectiveness; diagnosis and monitoring of clonal disorders such as paroxysmal nocturnal hemoglobinuria (PNH) and mastocytosis; evaluation of hematopoiesis or lymphopoiesis in different clinical conditions, e.g. in healthy individuals, after stem cell transplantation or gene therapy (using hematopoietic precursor cells as target); and evaluation of the composition and quality of cell products to be used for therapeutic purposes.

The conventional diagnostic process in flow cytometric immunophenotyping is typically based on the usage of panels of antibodies. At present different, overlapping panels of antibodies are recommended for specific applications. Such panels are driven either by the medical indication (e.g.: screening for cytopenias, characterization of lymphocytosis), by disease (e.g.: acute leukemia diagnosis, lymphoma diagnosis) or disease status (e.g.: diagnostic classification of ALL vs. monitoring of ALL for evaluation of treatment effectiveness). Examples of recommended antibody panels are the European Leukemia Net (ELN) (1), the 2006 Bethesda International Consensus (2) panels for different subtypes of hematological malignancies, the EGIL panels for lineage assignment and subclassification of acute leukemias (3), the European Myeloma Network (EMN) panels for diagnosis, classification and monitoring of plasma cell dyscrasias (4), the ERIC (5) and Matutes (6) score panels for immunophenotypic subclassification of chronic lymphocytic leukemia and hairy cell leukemia vs. other chronic lymphoproliferative disorders.

These recommended antibody panels are mostly comparable between different countries and study groups, but never fully identical. Importantly, no or limited information has been provided by the various networks and study groups on how the antibodies should preferably be combined into a panel of antibody reagents conjugated with specific fluorescence compounds. Only simple lists of antibodies have been proposed, even when diagnostic laboratories can simultaneously stain a sample aliquot with 2, 3, 4, 5, 6, 7, 8 or more antibodies conjugated with different fluorescent dyes having fluorescence emissions that can be measured separately. Variations between centres around the world are due to the usage of:

Comparable but not identical lists of antibodies and antibody clones;

The same antibodies conjugated with different fluorochromes that show different sensitivities. For example, an antibody reagent might provide a negative result if the antibody is combined with a low-sensitive fluorochrome, while a positive result could be obtained if an antibody reagent consisting of the same antibody combined with a different, more sensitive fluorochrome, is used to stain the same cells.

Simultaneous assessment of different combinations of antibody reagents.

Variable and frequently suboptimal or inappropriate strategies for the identification of the cell population(s) of interest, such as the CD45 gating in acute myeloblastic leukemias.

As a consequence, the seemingly comparable antibody panels do not result in comparable diagnosis of clinical samples. In fact, the reproducibility between diagnostic laboratories is not more than 70%. Unfortunately, diagnoses are missed because of inappropriate discrimination between normal and malignant cells or regenerating bone marrow is erroneously diagnosed as recurrence of acute leukemia.

In U.S. Pat. No. 5,047,321, Loken and Terstappen disclosed a procedure for the multiparameter analysis of cellular components in PB and BM. With the procedure described, these inventors could distinguish several cellular components of PB and BM, count the number of cells within each component, and provide a differential analysis of each of them based on the combined use of the LDS-751 (Exciton) DNA-dye, the thiazol orange (TO, Molecular Probes, Inc) RNA-dye, a fluorescently labeled anti-CD45 monoclonal antibody, forward light scatter (FSC) and sideward light scatter (SSC). This approach allowed the specific identification of nucleated red cells, erythrocytes, reticulocytes, platelets, lymphocytes, monocytes, neutrophilic granulocytes, basophilic granulocytes, eosinophilic granulocytes, and precursors of all nucleated hematopoietic cells. However, the described multiparameter analysis could not specifically differentiate between normal, reactive, regenerating and neoplastic cells coexisting in the same sample, neither could this procedure further characterize these groups of cells. A further refinement of this patent was described later on in U.S. Pat. No. 6,287,791 by Terstappen and Chen, but they did not show any improvement in characterizing the different populations of leukocytes.

More recently, Orfao et al. described in U.S. Pat. No. 7,332,295 a procedure for the multidimensional leukocyte differential analysis of PB, BM and other body fluids, which specifically allowed identification of dendritic cells and their subsets in addition to nucleated red cells, lymphocytes, monocytes, neutrophilic granulocytes, basophilic granulocytes, eosinophilic granulocytes and hematopoietic precursors of all nucleated cells. Furthermore, in U.S. Pat. No. 5,538,855, Orfao et al. described a procedure that allowed a more detailed analysis of the lymphoid compartments through the simultaneous identification of up to 12 different subsets of T, B and NK-cells in PB, BM and lymph node samples. In the patent, Orfao et al. used a combined staining for the CD3, CD19, CD56 (and/or CD16), CD4 and CD8 antigens in a 3-color single staining, where pairs of monoclonal antibodies conjugated with the same fluorochrome were used. Nevertheless, through this approach they could neither further characterize the identified cell subsets nor discriminate between normal and neoplastic cells; furthermore, some relevant subsets of lymphoid and non-lymphoid cells (e.g. the TCRγδ+ T-cells) present in a normal PB, BM or other tissues and body fluids, could not be specifically detected.

None of the referred procedures allowed directly for a more detailed characterization of the cells identified, including discrimination between normal, reactive, regenerating, and neoplastic/clonal cell populations. Such characterization and discrimination requires the use of a greater number of stainings associated with distinguishable fluorescence emissions and of flow cytometer instruments capable of measuring a higher number of different fluorescence emissions.

Many other publications show that, based on specific immunophenotypic profiles, normal cells can be discriminated from their neoplastic counterparts, and that the discrimination capabilities (sensitivity for discriminating normal from clonal/malignant cells) increase with the number of fluorochrome-conjugated antibody reagents used to stain the same sample. Some reports also show that normal and reactive cells as well as maturing cells during BM regeneration, may show distinct immunophenotypic profiles, but these cells could not be clearly discriminated from malignant cells. Importantly, panels of antibody combinations that have been proposed thus far can not efficiently discriminate between normal, reactive, regenerating cell populations and their neoplastic counterparts in a systematic way and, at the same time, allow for a clear-cut discrimination between different diagnostic disease categories through an extended immunophenotypic characterization of the malignant cells.

With the introduction of the new generation of multi-laser flow cytometers in diagnostic laboratories, the potential space for building different panels even with the same list of antibodies, has exponentially increased due to the possibility of using a larger number of different fluorescent compounds and simultaneously measure a higher number of fluorescence emissions in single cells. In U.S. Pat. No. 7,321,843, Orfao, Pedreira and Sobral da Costa propose a new approach based on mathematical calculation procedures (e.g. the closest neighbour principle), where flow cytometry list mode data files containing information for each single cell measured about an unlimited number of parameters could be generated, after several aliquots of a sample stained with different, partially overlapping, combinations of monoclonal antibodies had been measured in a flow cytometer. The utility of this procedure could only be maximised with the increased multicolour capabilities of the most recent flow cytometers. This is because these procedures require the design of efficient panels of combinations of monoclonal antibody reagents where common backbone markers are combined with other additional markers which vary for each combination of monoclonal antibodies in a panel. In parallel, the same authors also described (U.S. Pat. No. 7,507,548) a procedure for comparison of flow cytometry data from a case against a reference data file which would allow direct comparison of e.g. normal vs. neoplastic cells. However, in both patents, the authors failed to propose a comprehensive antibody panel that could be thoroughly and systematically applied to the diagnosis, classification, staging and/or monitoring of leukaemia, lymphoma and plasma cell dyscrasias.

Thus, existing protocols do not teach about how to specifically combine the widely recommended monoclonal antibodies in a panel; they propose different panels for the diagnostic classification and monitoring of minimal disease; they focus in single, uniform disease groups; they show a limited efficiency once widely tested; they do not provide a way for direct combination of the information measured for several aliquots from a single sample; and/or they have failed in systematically distinguishing normal/reactive versus clonal/neoplastic cells based on their immunophenotypic properties, in specific diseases such as chronic T and NK lymphoproliferative disorders (e.g. in the differential diagnoses of large granular lymphocytic leukemia).

The present inventors recognized these difficulties, and set out to design improved, well-defined antibody panels that avoid misinterpretation and over-interpretation of results. After careful selection of the relevant markers, design of appropriate combinations of antibodies in multicolor tubes, and the selection of suited fluorochromes (based on need for brightness, compensation, stability, etc.), a set of antibody reagents was developed. The studies were complemented with extensive multicentric evaluation of the consensus panels in order to reshape and achieve an optimal efficiency.

Accordingly, the invention provides in one embodiment a reagent composition for flow cytometric immunophenotyping of leukocytes comprising at least eight distinct fluorochrome-conjugated antibodies comprising a set of at least three identification antibodies for the identification of a leukocyte population of interest and at least four characterization antibodies for further characterization and/or classification of said leukocyte population. A reagent composition as provided herein comprises a panel of antibodies directed against one of the following combinations of markers: (a) CD20, CD4, CD45, CD19, Igλ, CD8, Igκ, CD56, TCRγδ, CD3 and CD38, wherein the antibody within either one of the pairs CD20/CD4, Igλ/CD8 and CD19/TCRγδ is conjugated to the same fluorochrome (LST reagent composition); (b) CD20, CD45, CD8, Igλ, CD56, Igκ, CD4, CD3, CD14 and CD38, wherein the antibody within either one of the pairs CD8/Igλ, CD56/Igκ and CD3/CD14 is conjugated to the same fluorochrome (SST reagent composition); (c) CD45, CD138, CD38, CD56, β2micro, CD19, cyIgκ and cyIgλ (PCST reagent composition) or (d) cyCD3, CD45, cyMPO, cyCD79a, CD34, CD19, CD7 and CD3 (ALOT reagent composition).

In a preferred embodiment, the composition comprises monoclonal antibodies. CD stands for cluster designation and is a nomenclature for the identification of specific cell surface antigens defined by monoclonal antibodies. Abbreviations used are as follows: cyIgκ=cytoplasmic IgG kappa chain; cyIgλ=cytoplasmic IgG lambda chain; β2micro=β$_2$ microglobulin; cyMPO=cytoplasmic myeloperoxidase. (Monoclonal) antibodies against the indicated markers can be commercially obtained from various companies, including Becton/Dickinson (BD) Biosciences, Dako, Beckman Coulter, CYTOGNOS, Caltag, Pharmingen, Exbio, Sanquin, Invitrogen, and the like.

Suitable fluorochromes for conjugating antibodies are known in the art. As will be understood, the fluorochromes used within a reagent composition should be distinguishable by flow cytometry. The fluorochromes are preferably selected for brightness, limited spectral overlap and limited need for compensation, stability, etc. The following panel of fluorochromes is of particular use in a reagent composition according to the invention: (1) pacific blue (PacB) or Horizon V450, (2) pacific orange (PacO) or AMCA, (3) fluorescein isothiocyanate (FITC) or Alexa488, (4) phycoerythrin (PE), (5) peridinin chlorophyll protein/cyanine 5.5 (PerCP-Cy5.5), PerCP or PE-TexasRed, (6) phycoerythrin/cyanine7 (PE-Cy7), (7) allophycocyanine (APC) or Alexa647, and (8) allophycocyanine/H7 (APC-H7), APC-Cy7, Alexa680 or Alexa700. After multiple testing rounds, the present inventors observed that very good results can be obtained if the following fluorochromes are chosen: Pacific Blue or Horizon V450, Pacific Orange, fluorescein isothiocyanate (FITC), phycoerythrin (PE), peridinin chlorophyll protein/cyanine 5.5 (PerCp-Cy5.5), PE-Cy7, allophycocyanine (APC), and APC-H7.

The expression "wherein the antibody within either one of the pairs is conjugated to the same fluorochrome" is meant to indicate that both antibodies of the first pair are conjugated to fluorochrome A and that both antibodies of the second pair are conjugated to fluorochrome B. Thus, within each pair the fluorochromes are the same but between different pairs the fluorochromes are distinguishable.

Each of the reagent compositions can be used as such, e.g. for the screening of a lymphoid disease. See FIG. 2 for a schematic overview of exemplary applications of the various reagent compositions. The invention thus also relates to diagnostic kits comprising one or more reagent compositions. However, the compositions are also advantageously used in combination with one or more further reagent compositions, in particular reagent compositions designed for the further screening and classification of the disease. The expression "in combination with" does not refer to the physical combination or mixing of the reagent compositions, but to their application in separate (consecutive) analysis steps and combination of the data thus obtained. For example, a screening tube used in combination with a characterization tube involves two separate analytical steps on separate aliquots of the same biological sample, each using one of the reagent compositions, followed by data recording and evaluation.

Therefore, the invention also relates to a set of at least two reagent compositions, said set comprising a reagent composition as described herein above, and at least one further reagent composition comprising distinct fluorochrome-conjugated antibodies. Thus, both reagent compositions comprise a distinct panel of antibodies, although some antibodies might be present in both compositions. It is very convenient if the panel of distinct fluorochromes is essentially the same for each of the reagent compositions, and that up to eight different fluorochromes are used in total.

In one embodiment, a set of at least two reagent compositions comprises a reagent composition according to (a) and/or (b) and/or (c) defined herein above (i.e. LST reagent and/or SST reagent and/or PCST reagent), together with at least one further reagent composition comprising distinct fluorochrome-conjugated antibodies, preferably directed against one of the following combinations of markers:
(i) CD20, CD45, CD23, CD10, CD79b, CD19, CD200 and CD43;
(ii) CD20, CD45, CD31, LAIR1, CD11c, CD19, IgM and CD81
(iii) CD20, CD45, CD103, CD95, CD22, CD19, CXCR5 and CD49d
(iv) CD20, CD45, CD62L, CD39, HLADR, CD19, CD27 and CD31

(v) CD4, CD45, CD7, CD26, CD3, CD2, CD28 and CD8
(vi) CD4, CD45, CD27, CCR7, CD3, CD45RO, CD45RA and CD8
(vii) CD4, CD45, CD5, CD25, CD3, CD11c and CD8
(viii) CD4, CD45, CD57, CD30, CD3, CD11c and CD8
(ix) CD4, CD45, cyPerforin, cyGranzyme, CD3, CD16, CD94 and CD8
(x) CD4, CD45, CD279, CD3 and CD8
(xi) CD2, CD45, CD7, CD26, CD3, CD66, CD5 and CD19
(xii) CD16, CD45, CD57, CD25, CD3, CD56, CD11c and CD19
(xiii) HLADR, CD45, cyPerforin, cyGranzyme, CD3, CD56, CD94 and CD19; or
(xiv) CD45, CD138, CD38, CD28, CD27, CD19, CD117 and CD81

In one embodiment, a set comprises both the LST and SST reagents and at least one of the above further reagents. In another embodiment, a set comprises at least the PCST reagent.

In another embodiment, a set of at least two reagent compositions comprising a first reagent composition according to (d) as defined herein above (ALOT reagent), and at least one further reagent composition comprising distinct fluorochrome-conjugated antibodies directed against one of the following combinations of markers:
(i) CD20, CD45, CD58, CD66c, CD34, CD19, CD10 and CD38
(ii) IgK, CD45, cyIgμ, CD33, CD34, CD19, IgM, CD117 and Igλ, wherein the antibodies against IgM and CD117 are conjugated to the same fluorochrome
(iii) CD9, CD45, terminal deoxynucleotidyl transferase (TdT), CD13, CD34, CD19, CD22 and CD24
(iv) CD21, CD45, CD15, CDw65, NG2, CD34, CD19, CD123 and CD81, wherein the antibodies against CD15 and CDw65 are conjugated to the same fluorochrome
(v) cyCD3, CD45, TdT, CD99, CD10, CD1a and CD3
(vi) cyCD3, CD45, CD2, CD117, CD4, CD8, CD7 and CD3
(vii) cyCD3, CD45, TCRγδ, TCRαβ, CD33, CD56, cyTCRβ and CD3
(viii) cyCD3, CD45, CD44, HLADR, CD45RA, CD123 and CD3
(ix) HLADR, CD45, CD16, CD13, CD34, CD117, CD11b and CD10
(x) HLADR, CD45, CD35, CD64, CD34, CD117, immune receptor expressed by myeloid cell 2 (IREM2) and CD14
(xi) HLADR, CD45, CD36, CD105, CD34, CD117, CD33 and CD71
(xii) HLADR, CD45, CD15, chondroitin sulfate proteoglycan (NG2), CD34, CD117, CD7 and CD38
(xiii) HLADR, CD45, CD42a, CD61, CD203c, CD34, CD117, CD123 and CD4, wherein the antibodies against CD42a and CD61 are conjugated to the same fluorochrome
(xiv) HLADR, CD45, CD41, CD25, CD34, CD117, CD42b and CD9
(xv) HLADR, CD45, CD41, CD25, CD34, CD117, CD42b and CD9; or
(xvi) HLADR, CD45, TdT, CD56, CD34, CD117, CD22 and CD19.

Exemplary sets of reagent compositions include at least one reagent composition as recited in Tables 1 and/or 6 herein below, together with at least one reagent composition as recited in any one of Tables 2-5 and 7-9.

A further aspect relates to a diagnostic kit for flow cytometric immunophenotyping of leukocytes, wherein the kit comprises one or more sets of at least two reagent compositions described above. The kit may in addition comprise other useful components, such as instructions for use, sample preparation reagent, buffer, and/or control samples.

Reagent compositions, sets and diagnostic kits provided herein find their application in various fields. For example, the proposed panels can be applied as a whole or only partially depending on the nature of the sample, medical indication or the specific goal. The panel may use specific monoclonal antibody reagents by a single or several different manufacturers, in combination with different cell preparation techniques for staining of cell surface only and/or cell surface plus intracellular markers. Similarly, the reagent compositions may be upgraded into a panel including combinations containing monoclonal antibody reagents conjugated with >8 different fluorochromes where the same backbone markers are maintained and combined with additional or similar markers. An antibody composition may also act as a core panel to which new combinations are added with different goals, including monitoring of the immune system.

In one embodiment, there is provided a diagnostic kit for the identification and characterization of mature lymphoid cells, comprising the SST and/or LST and/or PCST reagent composition together with at least one reagent composition for detecting B-cell chronic lymphoproliferative disorder (B-CLPD) comprising antibodies against CD20, CD45, CD23, CD10, CD79b, CD19, CD200 and CD43; CD20, CD45, CD31, LAIR1, CD11c, CD19, IgM and CD81; CD20, CD45, CD103, CD95, CD22, CD19, CXCR5 and CD49d; or CD20, CD45, CD62L, CD39, HLADR, CD19, CD27 and CD31.

For example, there is provided a diagnostic kit for the identification and characterization of mature lymphoid cells, comprising the SST and/or LST and/or the PCST reagent composition together with at least one reagent composition for detecting T-cell chronic lymphoproliferative disorder (T-CLPD) comprising antibodies against CD4, CD45, CD7, CD26, CD3, CD2, CD28 and CD8; CD4, CD45, CD27, CCR7, CD3, CD45RO, CD45RA and CD8; CD4, CD45, CD5, CD25, CD3, CD11c and CD8; CD4, CD45, CD57, CD30, CD3, CD11c and CD8; CD4, CD45, cyPerforin, cyGranzyme, CD3, CD16, CD94 and CD8; or CD4, CD45, CD279, CD3 and CD8.

Another exemplary diagnostic kit for the identification and characterization of mature lymphoid cells comprises the SST and/or LST and/or PCST reagent composition together with at least one reagent composition for detecting NK-cell chronic lymphoproliferative disorder (NK-CLPD) comprising antibodies against CD2, CD45, CD7, CD26, CD3, CD56, CD5 and CD19; CD16, CD45, CD57, CD25, CD3, CD56, CD11c and CD19; HLADR, CD45, cyPerforin, cyGranzyme, CD3, CD56, CD94 and CD19; CD45, CD138, CD38, CD56, β2micro, CD19, cyIgκ and cyIgλ; or CD45, CD138, CD38, CD28, CD27, CD19, CD117 and CD81.

In yet another embodiment, there is provided a diagnostic kit for the identification and characterization of mature lymphoid cells, comprising the SST and/or LST and/or PCST reagent composition together with at least one reagent composition for detecting plasma cell dyscrasias (PCD) comprising antibodies against CD45, CD138, CD38, CD56, β2micro, CD19, cyIgκ and cyIgλ; or CD45, CD138, CD38, CD28, CD27, CD19, CD117 and CD81.

Also provided is a diagnostic kit for identification and characterization of immature lymphoid cells, comprising the ALOT reagent composition together with at least one reagent composition for detecting B-cell precursor ALL (BCP-ALL) comprising antibodies against CD20, CD45, CD58, CD66c, CD34, CD19, CD10 and CD38; Igκ, CD45, cyIgμ, CD33, CD34, CD19, IgM, CD117 and Igλ, wherein the antibodies against IgM and CD117 are conjugated to the same fluorochrome; CD9, CD45, TdT, CD13, CD34, CD19, CD22 and CD24; or CD21, CD45, CD15, CDw65, NG2, CD34, CD19, CD123 and CD81, wherein the antibodies against CD15 and CDw65 are conjugated to the same fluorochrome.

In a further aspect, a diagnostic kit for identification and characterization of immature lymphoid cells comprises the ALOT reagent composition together with at least one reagent composition for detecting T-cell precursor ALL (T-ALL) comprising antibodies against cyCD3, CD45, TdT, CD99, CD10, CD1a and CD3; cyCD3, CD45, CD2, CD117, CD4, CD8, CD7 and CD3; cyCD3, CD45, TCRγδ, TCRαβ, CD33, CD56, TCR βF1 and CD3; or cyCD3, CD46, CD44, HLADR, CD45RA, CD123 and CD3.

In still a further aspect, a diagnostic kit is provided for identification and characterization of myeloid cells, comprising the ALOT reagent composition together with at least one reagent composition for detecting acute myeloid leukemia (AML), myelodysplastic syndrome (MDS)/chronic myeloproliferative disorder (MPD), comprising antibodies against HLADR, CD45, CD16, CD13, CD34, CD117, CD11b and CD10; HLADR, CD45, CD35, CD64, CD34, CD117, IREM2 and CD14; HLADR, CD45, CD36, CD105, CD34, CD117, CD33 and CD71; HLADR, CD45, CD15, NG2, CD34, CD117, CD7 and CD38; HLADR, CD45, CD42a, CD61, CD203c, CD34, CD117, CD123 and CD4, wherein the antibodies against CD42a and CD61 are conjugated to the same fluorochrome; HLADR, CD45, CD41, CD25, CD34, CD117, CD42b and CD9; HLADR, CD45, CD41, CD25, CD34, CD117, CD42b and CD9; or HLADR, CD45, TdT, CD56, CD34, CD117, CD22 and CD19.

The invention also relates to a method for flow cytometric immunophenotyping of leukocytes, comprising the steps of providing a biological sample comprising leukocytes and contacting at least a portion (aliquot) of the sample with a reagent composition provided herein. Any type of (human) sample known or suspected to contain leukocytes may be used. For example, the sample is peripheral blood, bone marrow, tissue sample such as lymph nodes, adenoid, spleen, or liver, or other type of body fluid such as cerebrospinal fluid, vitreous fluid, synovial fluid, pleural effusions or ascitis. Preferably, the method comprises contacting a first aliquot of said sample with a first reagent composition of a set according to the invention and contacting at least a second aliquot of said sample with a further reagent composition of said set; analyzing leukocytes in said aliquots in a flow cytometer; and storing and evaluating the data obtained. Typically, step (c) comprises the use of software for data integration and multidimensional analysis of flow cytometry files. Very suitable for use in a method of the invention is the software commercially available from CYTOGNOS SL (Salamanca, Spain) under the tradename INFINICYT™. The INFINICYT™ software can automatically combine the immunophenotypic information of the selected cell populations from multiple tubes according to the so-called nearest neighbor calculations in which individual cells from one aliquot of a sample are matched with corresponding individual cells from another aliquot of the same sample, according to their backbone markers and scatter profile. The INFINICYT procedure can transform the herein presented 8-color EuroFlow panels into 12, 16, or ≥20-color immunostainings, dependent on the number of tubes per panel and the number of backbone markers per tube. The antibody panels and the INFINICYT software can be used in combination with all currently available flow cytometers that allow 8-color immunostainings, such as FACSCanto™ II, FACSAria, LSRII, DAKO CyAn™, Gallio, etc.

LEGEND TO THE FIGURES

FIG. 1. Composition of three Categories of antibody panels

Figure 2:
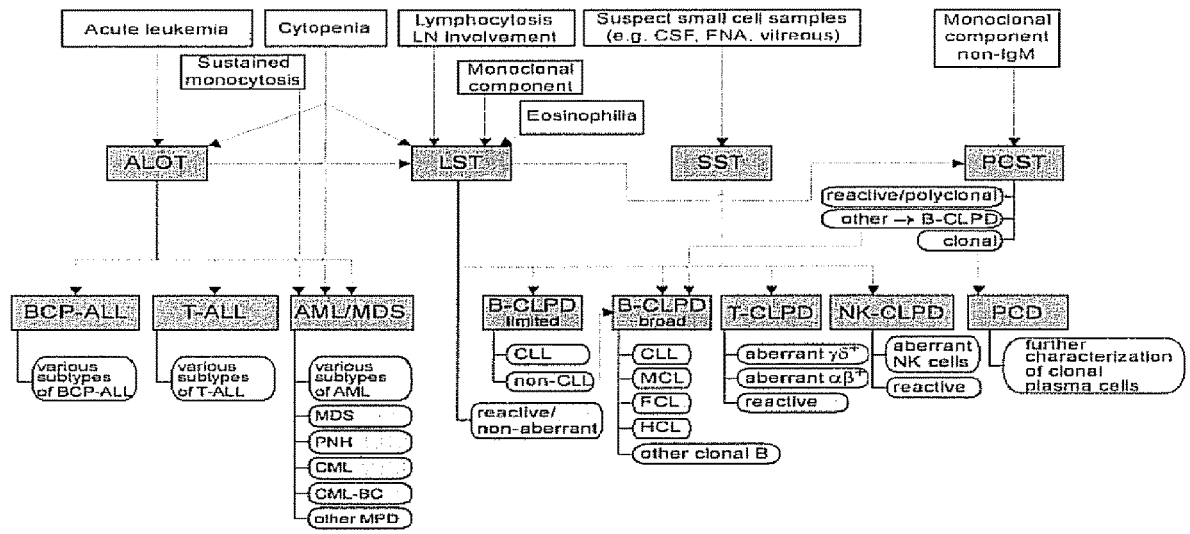

FIG. 2. Diagnostic flow diagram showing potential applications of the EuroFlow antibody panels.

DETAILED DESCRIPTION

1. Introduction

The present study was performed by the The EuroFlow Consortium (LSHB-CT-2006-018708) who initiated the project "Flow Cytometry for Fast and Sensitive Diagnosis and Follow-up of Haematological Malignancies", which includes the design of standardized multicolor immunophenotyping protocols for diagnosis, classification, and monitoring of leukemias, lymphomas and plasma cell dyscrasias. A key innovative component of these protocols are the EuroFlow panels of antibody combinations (EuroFlow panels). This EuroFlow invention relates among others to panels of combinations of antibody reagents (reagent compositions), which can be used to define normal, reactive, regenerating and malignant hematopoietic cells in a standardized way. As such, they allow for a comprehensive immunophenotypic diagnosis, classification, staging and monitoring of both chronic and acute leukemias, myelodysplastic syndromes, myeloproliferative disorders, mastocytosis, paroxysmal nocturnal haemoglobinuria, lymphomas and plasma cell dyscrasias. For the first time, the proposed panels are not based on subjective expert opinions, but they have been tested prospectively and modified for improving the answer to the most frequent medical indications of flow cytometry immunophenotyping. In turn, these panels are designed in an innovative way to be applied in combination with both conventional data analysis approaches and new interactive and semi-automated data analysis procedures in which information on single cells is combined for all parameters derived from the measurement of staining a sample with the antibody panel.

In order to establish these panels, the following sequential steps were performed:

1. Evaluation of all relevant markers used in the field for their usefulness or added value
   Markers proposed by European networks, such as ELN, EMN, ERIC;
   Markers proposed by the 2006 Bethesda International Consensus in US;
   New markers for mature B-cell malignancies as proposed by Rawstron et al.
2. Design and selection of combinations of markers (≥6), which can recognize normal vs. reactive vs. regenerating vs. abnormal/malignant cells within a specific compartment of hematopoietic cells (cell lineage, differentiation pathway, maturation stage and/or functional subset).
3. Evaluation of the proposed panels of combinations of antibody reagents in primary samples from healthy subjects and patients.
4. Repeated testing and optimization of the combinations of antibody reagents (choice of marker, choice of antibody clone, and choice of fluorochrome) based on uncommitted goals and room for improvement.
5. Evaluation of the optimized versions of the EuroFlow panels on large series of well-defined patient samples and samples from healthy controls.

Compared with pre-existing knowledge, this is the first design of a comprehensive panel (after prospectively evaluated in a multicentric way), which allows both discrimination between normal, reactive, regenerating and clonal/neoplastic cells and classification, staging and monitoring of clonal/neoplastic haematopoietic disorders, providing a clear indication about: 1) those markers required to be stained in common for appropriate and reproducible identification of all cell populations of interest in all stained aliquots of a sample, and 2) how they should be combined with further characterization markers in specific combinations of fluorochrome-conjugated antibody reagents. In addition, information about the goals of each combination is also given as indication about when and how to apply it. The invention was made only after extensive antibody panel testing and several redesigning cycles.

The EuroFlow panels of reagents are composed of subsets of one or multiple combinations (named tubes) of antibodies conjugated with eight or more fluorescent compounds, each of said combinations of reagents having different goals. The EuroFlow panels consist of three different categories: Category 1, Category 2 and Category 3 antibody panels (FIG. 1).

2. Categories of Antibody Panels

The following purposes are pursued by the EuroFlow panels of antibody combinations:

The Category 1 antibody panels aim at identification and characterization of different subsets of mature lymphoid cells, including normal, reactive, regenerating and neoplastic B-, T-, NK-cells and plasma cells, particularly in samples where a clonal and/or neoplastic lymphoid disorder is suspected because of e.g. lymphocytosis, lymph node enlargement, splenomegaly, monoclonal serum component, unexplained neurological symptoms, etc. The Category 2 antibody panels aim at identification and characterization of normal, reactive, regenerating and neoplastic immature (or early maturing) T- and/or B-lymphoid cells, particularly in samples suspected of containing neoplastic lymphoid precursors. The Category 3 antibody panels aim at identification and characterization of normal, reactive, regenerating and neoplastic immature, maturing and matured myeloid cells, particularly in samples suspected of containing neoplastic myeloid cells or neoplastic cells expressing myeloid-associated markers. Within each of said three Categories, some of the combinations of antibody reagents are aimed to be used in a single-tube screening step with more broad aims, while others are more likely applied in multi-tube classification steps when more specific target populations have already been identified in the screening step.

2.1 Category 1 Antibody Panels

The Category 1 antibody panels are composed of three screening tubes aimed at the initial identification and characterization of the specific subgroups of mature lymphoid cells present in samples which contain normal or high cell counts (e.g. normal peripheral blood) and low cell counts (e.g. vitreous humor), respectively, and four different sets of multi-tube antibody combinations aiming at further characterization of B-, T-, NK-cells and plasma cells. The Category 1 screening tubes may be used to screen for the presence of clonal and neoplastic T, B- or NK-cells and plasma cells in samples with relatively high and low cell counts, respectively. Typical examples of low cell count samples are fine needle aspirates (FNA), cerebrospinal fluid (CSF), and vitreous humor.

The above mentioned screening tubes are now termed as lymphoid screening tube for high cell count samples (abbreviated as LST), small sample tube (SST) for low cell count samples, and a separate plasma cell screening tube (PCST). In turn, the other four sets of tubes are devoted, among other uses, to further characterize the identified clonal or neoplastic B-, T-, NK-cells and plasma cells in patients with different B-, T- and NK-cell chronic lymphoproliferative disorders (abbreviated as BCLPD, TCLPD and NKCLPD, respectively) and plasma cell dyscrasias (abbreviated as PCD), respectively.

2.2 Category 2 Antibody Panels

The Category 2 antibody panels consist of a screening tube devoted to the initial identification and characterization of immature lymphoid vs. non-lymphoid precursors, and two sets of tubes for further detailed characterization of B-cell and T-cell precursors. Among other applications, the screening tube may be used for the classification of acute leukemias into lymphoid vs. non-lymphoid versus undifferentiated versus biphenotypic or bilineage acute leukemias. This tube might also be used for the discrimination between normal/regenerating and neoplastic/malignant B-cell precursors in the bone marrow, peripheral blood and other tissues and T-cell precursors in the thymus, respectively. Consequently, this screening tube is now termed as acute leukemia orientation tube (abbreviated ALOT). The other two sets of tubes may be used, among other applications, for the characterization of lymphoid blast cells showing B-cell and T-cell commitment in patients with B-cell precursor acute lymphoblastic leukemia (BCP-ALL) and T-ALL as well as in patients with acute leukemia showing an undifferentiated or biphenotypic/bilineage phenotype.

2.3 Category 3 Antibody Panels

Finally, the Category 3 antibody panels are composed of a screening tube which aims at discriminating between lymphoid and non-lymphoid precursor cells and which is identical to the screening tube described above in Category 2 (ALOT tube), and one additional set of tubes aiming at the characterization of maturing non-lymphoid cells from the earliest hematopoietic precursors to mature myeloid cells, including the different maturation stages of cells committed to the erythroid, megakaryocytic, monocytic, neutrophilic, eosinophilic, basophilic, mast cell and dendritic cell lineages as well as the more immature, uncommitted hematopoietic precursors and stromal cells in case they are present in the sample (e.g. in BM). Among other uses, this set of tubes may be applied for the characterization of neoplastic/clonal diseases and other disorders in which the cells of interest (e.g.: clonal/neoplastic, altered/aberrant cells) display myeloid differentiation such as in patients with acute myeloid leukemia (AML), myelodysplastic syndrome (MDS), chronic myeloproliferative disorder (MPD), paroxysmal nocturnal haemoglobinuria (PNH), mastocytosis, idiopathic cytopenia of undetermined significance (ICUS)- and/or acute leukemia with myeloid-associated markers as it occurs in biphenotypic and bilineage acute leukemias. This group of tubes is abbreviated from now on as AML/MDS/MPD.

2.4 Types of Markers Used in EuroFlow Panels

In each tube of the EuroFlow panels, two types of antibody reagents are combined: 1) reagents which mainly aim at identifying the precise cell populations of interest present in the sample (Backbone markers), which also provide additional information about the phenotypic characteristics of said cell populations, and; 2) reagents mainly devoted to further characterization/classification of said cell populations as well as other groups of cells in the sample (Characterization markers).

Typically, backbone markers are repeated in each tube of the following sets of tubes: AML/MDS/MPD, BCP-ALL, T-ALL, B-CLPD, T-CLPD, NK-CLPD, PCD). In addition, backbone markers of the B-CLPD set of tubes are also common to the LST and SST screening tubes, backbone markers of the PCD set of tubes are common to the PCST, and backbone markers of the BCP-ALL and the T-ALL sets of tubes are also common to the ALOT; finally, two of the backbone markers in the AML panel (i.e.: CD34 and CD45) are also common to the ALOT tube.

In turn, characterization markers are combined in a comprehensive way in each tube, so that they would allow distinguishing normal, reactive regenerating vs clonal/neoplastic cells, even when present in low numbers and in case of neoplastic cells they would allow further diagnosis, subclassification, staging and monitoring of acute and chronic leukemias, lymphomas and plasma cell dyscrasias. For this purpose in multi-tube panels, each tube is devoted to a specific aim related to full characterization and monitoring of a disease entity if combined with the information from the corresponding screening tube (e.g. for the diagnosis, staging and monitoring of CLL, tube #4 of the B-CLPD multi-tube panel in combination with the LST will suffice) or for specific disease-associated information (e.g. tube #24 in the BCP-ALL multi-tube panel shown in Table 7 is specifically devoted for distinguishing between normal/reactive and regenerating versus malignant B-cell precursors and minimal residual disease monitoring in BCP-ALL).

2.5 INFINICYT Software Tools for Optimal Application of the EuroFlow Panels

The antibody panels according to the invention can be used in combination with the INFINICYT software tools which are commercially available. The software is based on recently described procedures for generating files with an unlimited number of parameters through merging data files and calculating the information derived from the measurement of markers in one sample aliquot to the individual cells measured in other aliquots of the same sample, using different combinations of antibody reagents which only have partial overlap (U.S. Pat. No. 7,321,843), as well as for comparisons between different samples or different groups of samples (U.S. Pat. No. 7,507,548).

3. Composition of the Category 1 Antibody Panels for Mature Lymphoid Cells

In the multi-tube combinations of antibody reagents of the Category 1 antibody panels for mature lymphoid cells the selected common backbone markers vary between the four different panels and consist of (antibody CD plus fluorochrome compound number): 1) CD20-1, CD45-2 and CD19-6 for B-CLPD; 2) CD4-1, CD45-2, CD3-5 and CD8-8 for T-CLPD; 3) CD45-2, CD3-5, CD56-6 and CD19-8 for NK-CLPD, and; 4) CD45-1, CD138-2, CD38-3 and CD19-6 for PCD. In addition, the backbone markers used in the B-CLPD tube are also used in the LST and SST screening tubes, and the backbone markers of the PCD tubes are also used in the PCST.

The backbone markers in each of those multi-tube combinations of antibody reagents aim at providing delineation of the groups of cells of interest and the specific identification of neoplastic cells in diagnostic and follow-up samples containing enough numbers of tumor cells. In addition, for each of the four multi-tube combinations, backbone markers are combined with a variable number of additional characterization markers which further contribute to the discrimination between normal, reactive, regenerating and neoplastic/clonal B-, T, NK-cells and plasma cells, respectively, even when these are present in minimal numbers (e.g. minimal residual disease monitoring and disease staging), as well as for the distinction between clonal/neoplastic cells from different disease categories.

3.1. The Lymphoid Screening Tube (LST), the Small Sample Tube (SST), and the Plasma Cell Screening Tube (PCST)

The EuroFlow LST reagent composition was designed and approved for evaluation of several suspected clinical conditions, such as lymphocytosis, lymph node enlargement, splenomegaly, monoclonal serum components, unexplained neurological symptoms, unexplained cytopenias, etc. (FIG. 2). The composition of an exemplary LST tube is provided in Table 1. This tube detects aberrant mature lymphocyte populations of B, T and NK lineage. However, this 8-color tube does not allow the precise diagnosis and classification of the detected aberrant lymphocyte populations. This typically needs further characterization with the B-CLPD, T-CLPD, NK-CLPD and/or PCD tubes (see Sections 3.2, 3.3 and 3.4).

The EuroFlow SST reagent composition is a modified version of EuroFlow LST, specially designed for evaluation of small samples and samples with (very) low cell counts, such as fine needle aspirates (FNA), cerebrospinal fluid (CSF), vitreous humor, etc. For this special aim, the tube allows the unequivocal recognition of normal leukocytes present in these samples, e.g. B, T, NK cells and monocytes as well as any coexisting aberrant cell population. The composition of an exemplary SST reagent is provided in Table 1.

The EuroFlow PCST reagent composition is specially designed for screening of plasma cells in order to detect aberrancies or clonality. In case of aberrant or clonal plasma cells, complementary phenotypic characterization is achieved via the 2-tube PCD antibody panel.

In any of the Tables of the present application, fluorochrome number 1 corresponds to pacific blue (PacB) or Horizon V450, number 2 to pacific orange (PacO) or AMCA, number 3 to fluorescein isothiocyanate (FITC) or Alexa488, number 4 to phycoerythrin (PE), number 5 to peridinin chlorophyll protein/cyanine 5.5 (PerCP-Cy5.5), PerCP or PE-Texas Red, number 6 to phycoerythrin/cyanine7 (PE-Cy7), number 7 to allophycocyanine (APC) or Alexa647, and number 8 to allophycocyanine/H7 (APC-H7), APC-Cy, Alexa680 or Alexa700. A preferred combination is pacific blue (PacB), pacific orange (PacO), fluorescein isothiocyanate (FITC), phycoerythrin (PE), peridinin chlorophyll protein/cyanine 5.5 (PerCP-Cy5.5), phycoerythrin/cyanine7 (PE-Cy7), allophycocyanine (APC), and allophycocyanine/H7 (APC-H7).

TABLE 1

Single tube EuroFlow screening combinations for normal and malignant/aberrant mature lymphoid cells

| Tube# | Fluorochrome | | | | | | | |
|---|---|---|---|---|---|---|---|---|
| | 1 | 2 | 3 | 4 | 5 | 6 | 7 | 8 |
| 1 (LST) | $CD20^{BB}$ and CD4 | $CD45^{BB}$ | Igλ and CD8 | Igκ and CD56 | CD5 | $CD19^{BB}$ and TCRγδ | CD3 | CD38 |
| 2 (SST) | $CD20^{BB}$ | $CD45^{BB}$ | CD8 and Igλ | CD56 and Igκ | CD4 | $CD19^{BB}$ | CD3 and CD14 | CD38 |
| 3 (PCST) | $CD45^{BB}$ | $CD138^{BB-}$ | $CD38^{BB}$ | CD56 | β2micro | $CD19^{BB}$ | CyIgκ | CyIgλ |

$^{BB}$= These markers act as Backbone markers when LST or SST results are combined with the results obtained with multi-tube EuroFlow classification combination for B-CLPD (see Table 2) or when the PCST results are combined with the results obtained with the 2-tube EuroFlow classification combination for PCD (see Table 5); LST = lymphoid screening tube; SST = small sample tube; PCST = plasma cell screening tube.

3.2. The Multi-Tube Antibody Panel for B-Cell Chronic Lymphoproliferative Disorders (B-CLPD)

The B-CLPD is designed to classify mature B-cell malignancies according to WHO entities based on flow cytometric data only (see Table 2). Information obtained using the LST simultaneously or sequentially has to be integrated into the B-CLPB panel (e.g. via INFINICYT software). The B-CLPD panel is designed to work in cases in which the malignant B cell population can be purified to >90% using the backbone markers CD20, CD19, and CD45, regardless of the cell material analyzed.

The panel is designed to work in a modular way, i.e. it is not necessary to stain the whole panel if the pre-test probability for a particular B-cell malignancy is high. In those instances the panel will allow to diagnose a particular entity using a reduced number of tubes. For example, the LST tube #1 plus tube #5 are sufficient to diagnose CLL with a very high positive predictive value (PPV).

TABLE 2

Multi-tube EuroFlow classification combinations for B-cell chronic lymphoproliferative disorders (B-CLPD)

| Tube# | 1 | 2 | 3 | 4 | 5 | 6 | 7 | 8 | Aim |
|---|---|---|---|---|---|---|---|---|---|
| 4 | $CD20^{BB}$ and CD4 | $CD45^{BB}$ | Igλ and CD8 | Igκ and CD56 | CD5 | $CD19^{BB}$ and TCRγδ | CD3 | CD38 | LST: Detection of (almost) all mature B-cell malignancies |
| 5 | $CD20^{BB}$ | $CD45^{BB}$ | CD23 | CD10 | CD79b | $CD19^{BB}$ | CD200 | CD43 | Identification, of all CLL cases |
| 6 | $CD20^{BB}$ | $CD45^{BB}$ | CD31 | LAIR1 | CD11c | $CD19^{BB}$ | IgM | CD81 | Identification of all HCL cases; characterization of benign B-, T-, NK-cells |
| 7 | $CD20^{BB}$ | $CD45^{BB}$ | CD103 | CD95 | CD22 | $CD19^{BB}$ | CXCR5 | CD49d | Identification of DLBCL, FL, MZL, LPL |
| 8 | $CD20^{BB}$ | $CD45^{BB}$ | CD62L | CD39 | HLADR | $CD19^{BB}$ | CD27 | CD31 | Identification of DLBCL, FL, MZL, LPL |

$BB$ = Backbone marker; Tube 4 is identical to the LST (see Table 1). The described tubes can also be successfully applied for disease staging and monitoring.

3.3. The Multi-Tube Antibody Panel for T-Cell Chronic Lymphoproliferative Disorders (T-CLPD)

The EuroFlow T-CLPD aims for diagnosis and classification of mature T-cell malignancies. Also for this panel, information obtained with the LST simultaneously and sequentially is preferably integrated with T-CLPD tubes (e.g., via harmonization with the INFINICYT software). The panel is designed to work in cases in which the malignant T cell population can be purified to >90% using the backbone-markers CD3, CD4, CD8, and CD45, regardless of the cell material analyzed. The combination of LST and T-CLPD tubes can detect T-cell malignancies of both TCRαβ and TCRγδ lineages.

TABLE 3

Multi-tube EuroFlow classification combinations for T-cell chronic lymphoproliferative disorders (T-CLPD)

| Tube# | 1 | 2 | 3 | 4 | 5 | 6 | 7 | 8 | Aim |
|---|---|---|---|---|---|---|---|---|---|
| 9 | $CD4^{BB}$ | $CD45^{BB}$ | CD7 | CD26 | $CD3^{BB}$ | CD2 | CD28 | $CD8^{BB}$ | Phenotypic characterization; Identification of Sezary syndrome |
| 10 | $CD4^{BB}$ | $CD45^{BB}$ | CD27 | CCR7 | $CD3^{BB}$ | CD45RO | CD45RA | $CD8^{BB}$ | Phenotypic characterization; Assessment of maturation stage |
| 11 | $CD4^{BB}$ | $CD45^{BB}$ | CD5 | CD25 | $CD3^{BB}$ | HLADR | cyTCL1 | $CD8^{BB}$ | Phenotypic characterization; Identification of T-PLL |
| 12 | $CD4^{BB}$ | $CD45^{BB}$ | CD57 | CD30 | $CD3^{BB}$ | | CD11c | $CD8^{BB}$ | Phenotypic characterization; Cytotoxic phenotype and identification of anaplastic lymphoma |
| 13 | $CD4^{BB}$ | $CD45^{BB}$ | cyPerforin | cyGranzyme | $CD3^{BB}$ | CD16 | CD94 | $CD8^{BB}$ | Phenotypic characterization; Assessment of cytotoxic-associated phenotypes; Identification of T-LGL |
| 14 | $CD4^{BB}$ | $CD45^{BB}$ | | CD279 | $CD3^{BB}$ | | | $CD8^{BB}$ | Identification of lymphomas derived from follicular helper T cells (angioimmunoblastic T cell lymphomas) |

$BB$ = Backbone marker; the tubes can also be successfully applied for disease staging and monitoring.

3.4. The Multi-Tube Antibody Panel for NK-Cell Chronic Lymphoproliferative Disorders (NK-CLPD)

The EuroFlow NK-CLPD tube aims at the discrimination between aberrant and normal/reactive NK-cells. The NK-CLPD panel uses four Backbone markers: CD45-2, CD3-5, CD56-6 and CD19-8. (NK-CLPD)

TABLE 4

Multi-tube EuroFlow classification combinations for NK-cell chronic lymphoproliferative disorders (NK-CLPD)

| Tube# | 1 | 2 | 3 | 4 | 5 | 6 | 7 | 8 | Aim; MRD |
|---|---|---|---|---|---|---|---|---|---|
| 15 | CD2 | CD45$^{BB}$ | CD7 | CD26 | CD3$^{BB}$ | CD56$^{BB}$ | CD5 | CD19$^{BB}$ | Detection of aberrant NK cell phenotype |
| 16 | CD16 | CD45$^{BB}$ | CD57 | CD25 | CD3$^{BB}$ | CD56$^{BB}$ | CD11c | CD19$^{BB}$ | Detection of aberrant NK cell phenotype |
| 17 | HLADR | CD45$^{BB}$ | cyPerforin | cyGranzyme | CD3$^{BB}$ | CD56$^{BB}$ | CD94 | CD19$^{BB}$ | Detection of aberrant NK cell phenotype; Assessment of cytotoxic effector phenotype |

$^{BB}$= Backbone marker; the tubes can also be successfully applied for disease staging and monitoring.

3.5. The Multi-Tube Antibody Panel for Plasma Cell Dyscrasias (PCD)

The EuroFlow PCD panel comprises two tubes with four Backbone markers: CD45-1, CD138-2, CD38-3 and CD19-6 for PCD. (Table 5); tube #18 is identical to the PCST (tube #3) in Table 1. The PCD panel aims at the identification and enumeration of plasma cells as well as at the discrimination between normal polyclonal plasma cells such as in reactive plasmacytosis versus aberrant monoclonal plasma cells such as in monoclonal gammopathies of undetermined significance (MGUS), smoldering and symptomatic multiple myeloma (MM), plasma cell leukemias (PCL), amyloidosis, and extramedullary plasmacytoma, and the differential diagnosis among these plasma cell dyscrasias. In combination with the EuroFlow LST and B-CLPD panels, this multi-tube antibody panel will also contribute to the diagnosis of other plasma cell dyscrasias such as Waldenstrom's macroglobulinemia and lymphoplamacytic lymphoma (LPL).

TABLE 5

Multi-tube EuroFlow classification combinations for plasma cell dyscrasias (PCD)

| Tube# | 1 | 2 | 3 | 4 | 5 | 6 | 7 | 8 | Aim; |
|---|---|---|---|---|---|---|---|---|---|
| 18 | CD45$^{BB}$ | CD138$^{BB}$ | CD38$^{BB}$ | CD56 | β2micro | CD19$^{BB}$ | cyIgκ | cyIgλ | PCST: Detection of aberrant and clonal plasma cells |
| 19 | CD45$^{BB}$ | CD138$^{BB}$ | CD38$^{BB}$ | CD28 | CD27 | CD19$^{BB}$ | CD117 | CD81 | Complementary phenotypic characterization and evaluation of markers with potential prognostic impact |

$^{BB}$= Backbone marker. The described tubes can also be successfully applied for disease staging and monitoring; Tube #18 is identical to the PCST (Tube #3 in Table 1).

4. Composition of the Category 2 Panel for Immature Lymphoid Cells

4.1. The Acute Leukemia Orientation Tube (ALOT)

The EuroFlow ALOT tube was designed for assessment of the nature of immature blast cell populations in acute leukemia patients (B, T versus non-lymphoid, undifferentiated or mixed phenotype acute leukemias) and consequent orientation towards the most appropriate complementary antibody panel(s): BCP-ALL, T-ALL, and/or AML/MDS/MPD. The composition of the ALOT tube is provided in Table 6; the markers CD45-2, CD34-5 and CD19-6 act as backbone markers when the information of the ALOT is combined with the BCP-ALL panel (e.g.: using the INFINI-CYT software) and the cyCD3-1, CD45-2 and CD3-8 markers act also as common backbone markers when the information of the ALOT is combined with the T-ALL panel; in addition CD45-2 and CD34-5 are also common backbone markers to the AML/MDS/MPD multi-tube panel

TABLE 6

Single tube EuroFlow combination for lineage assignment of blast cells in acute leukemias

| Tube# | 1 | 2 | 3 | 4 | 5 | 6 | 7 | 8 |
|---|---|---|---|---|---|---|---|---|
| 20 (ALOT) | cyCD3$^{BB}$ | CD45$^{BB}$ | cyMPO | cyCD79a | CD34$^{BB}$ | CD19$^{BB}$ | CD7 | CD3$^{BB}$ |

$^{BB}$= These markers act as Backbone markers when results are combined with the results obtained with multi-tube EuroFlow classification combinations for BCP-ALL or T-ALL (see Table 7 and Table 8, respectively);

The ALOT is not suitable for exclusion of a hematological malignancy, because the ALOT antibody combination is not sufficient for that purpose. However, when the ALOT is combined with the LST and 4 tubes of the AML/MDS protocol (tube #29, 30, 31 and 32), virtually all types of hematological malignancies can be detected (not classified) or excluded (FIG. 2).

4.2. The Multi-Tube Antibody Panel for B-Cell Precursor Acute Lymphoblastic Leukemia (BCP-ALL)

The EuroFlow BCP-ALL tube aims at the recognition and classification of all classically defined BCP-ALL (pro-B-ALL, common-ALL, pre-B-ALL) or alternative BCP-ALL classifications, including immunophenotypic classifications associated with well-defined molecular aberrations, such as specific fusion genes. The information obtained with the BCP-ALL tube set needs to be combined with ALOT, based on the backbone markers CD45-2, CD34-5 and CD19-6 and using appropriate data analysis software (e.g. via the INFINICYT software) (Table 7).

TABLE 7

Multi-tube EuroFlow classification combinations for B-cell precursor ALL (BCP-ALL)

| Tube# | 1 | 2 | 3 | 4 | 5 | 6 | 7 | 8 | Aim |
|---|---|---|---|---|---|---|---|---|---|
| 21 | CD20 | CD45$^{BB}$ | CD58 | CD66c | CD34$^{BB}$ | CD19$^{BB}$ | CD10 | CD38 | Diagnosis and classification of BCP-ALL; Detection of LAP markers |
| 22 | Igκ | CD45$^{BB}$ | CyIgμ | CD33 | CD34$^{BB}$ | CD19$^{BB}$ | IgM and CD117 | Igλ | Diagnosis and classification of BCP-ALL; Detection of phenotypes assicieted with molecular aberrations |
| 23 | CD9 | CD45$^{BB}$ | TdT | CD13 | CD34$^{BB}$ | CD19$^{BB}$ | CD22 | CD24 | Diagnosis and classification of BCP-ALL; Detection of phenotypes assicieted with molecular aberrations; Detection of LAP markers |
| 24 | CD21 | CD45$^{BB}$ | CD15 and CDw65 | NG2 | CD34$^{BB}$ | CD19$^{BB}$ | CD123 | CD81 | Subclassification of BCP-ALL; Detection of LAP markers |

$^{BB}$= Backbone markers. The tubes can also be successfully applied for disease staging and monitoring.

4.3. The Multi-Tube Antibody Panel for T-Cell Acute Lymphoblastic Leukemia (T-ALL)

The EuroFlow T-ALL panel consists of four tubes and uses cyCD3-1, CD45-2, and CD3-8 as backbone markers (see Table 8) in common with the ALOT. The T-ALL panel aims at the recognition and classification of all classically defined T-ALL (immature T-ALL, common thymocytic T-ALL, mature T-ALL) or alternative T-ALL classification, e.g. based on TCR protein expression (cyTCRβ, TCRαβ, TCRγδ) or based on association with well-defined molecular aberrations.

TABLE 8

Multi-tube EuroFlow classification combinations for T-ALL

| Tube# | 1 | 2 | 3 | 4 | 5 | 6 | 7 | 8 | Aim |
|---|---|---|---|---|---|---|---|---|---|
| 25 | cyCD3$^{BB}$ | CD45$^{BB}$ | TdT | CD99 | CD5 | CD10 | CD1a | CD3$^{BB}$ | Diagnosis of T-ALL; Identification of LAP markers |

TABLE 8-continued

Multi-tube EuroFlow classification combinations for T-ALL

| Tube# | 1 | 2 | 3 | 4 | 5 | 6 | 7 | 8 | Aim |
|---|---|---|---|---|---|---|---|---|---|
| 26 | cyCD3[BB] | CD45[BB] | CD2 | CD117 | CD4 | CD8 | CD7 | CD3[BB] | Diagnosis of T-ALL, classification of T-ALL, and determine the maturation stage of arrest; Identification of LAP markers |
| 27 | cyCD3[BB] | CD45[BB] | TCRγδ | TCRαβ | CD33 | CD56 | Cy TCRβ | CD3[BB] | Diagnosis of T-ALL and determine the maturation stage of arrest; Identification of LAP markers |
| 28 | cyCD3[BB] | CD45[BB] | CD44 | CD13 | HLADR | CD45RA | CD123 | CD3[BB] | Subclassification of T-ALL |

[BB]= Backbone markers. The tubes can also be successfully applied for disease staging and monitoring.

5. Composition of the Category 3 Panel for Myeloid Cells

The EuroFlow AML/MDS/MPD panel comprises two complementary marker combinations (tubes 29-32 and tubes 32-35; see Table 9), all of them containing HLADR-1, CD45-2, CD34-5 and CD117-6 as backbone markers (Table 9). The first set of tubes (tubes 29-32) is designed to preferably be used in combination with EuroFlow ALOT in order to aim at the detection and classification (lineage assignment and maturation) of myeloid malignancies, such as in AML and MDS, with a major focus on immature neutrophilic lineage (tube 30), monocytic lineage (tube 31), and erythroid lineage (tube 32). These four tubes also contribute to the detection of APL (tube 32), PNH (tubes 29 and 30) and other aberrant myeloid phenotypes.

The second set of tubes (tubes 33-35) provides additional information about megakaryocytic, basophilic, plasmacytoid dendritic lineages (tube 33), as well as relevant information for the diagnosis of mastocytosis in association (or not) with AML/MDS (tube 34). Tube 35 further characterizes AML/MDS, and it is particularly focused on the aberrant expression of lymphoid-associated markers and abnormal lymphoid maturation.

REFERENCES

1.—Consensual European Immunophenotyping panels for leukemia. www.leukemia-net.org/content/home/.
2.—Wood B L, Arroz M, Barnett D, DiGiuseppe J, Greig B, Kussick S J, Oldaker T, Shenkin M, Stone E, Wallace P. 2006 Bethesda International Consensus recommendations on the immunophenotypic analysis of hematolymphoid neoplasia by flow cytometry: optimal reagents and reporting for the flow cytometric diagnosis of hematopoietic neoplasia. Cytometry B Clin Cytom. 2007; 72 Suppl 1:S14-22.
3.—Bene M C, Castoldi G, Knapp W, Ludwig W D, Matutes E, Orfao A, van't Veer M B. Proposals for the immunological classification of acute leukemias. European Group for the Immunological Characterization of Leukemias (EGIL). Leukemia. 1995; 9:1783-6
4.—Rawstron A C, Orfao A, Beksac M, Bezdickova L, Brooimans R A, Bumbea H, Dalva K, Fuhler G, Gratama J, Hose D, Kovarova L, Lioznov M, Mateo G, Morilla R, Mylin A K, Omedé P, Pellat-Deceunynck C, Perez Andres M, Petrucci M, Ruggeri M, Rymkiewicz G, Schmitz A,

TABLE 9

Multi-tube EuroFlow classification combinations for AML/MDS/MPD

| Tube# | 1 | 2 | 3 | 4 | 5 | 6 | 7 | 8 | Aim |
|---|---|---|---|---|---|---|---|---|---|
| 29 | HLADR[BB] | CD45[BB] | CD16 | CD13 | CD34[BB] | CD117[BB] | CD11b | CD10 | Diagnosis of AML |
| 30 | HLADR[BB] | CD45[BB] | CD35 | CD64 | CD34[BB] | CD117[BB] | IREM2 | CD14 | Diagnosis and subclassification of AML and PNH especially focussed on neutrophilic lineage |
| 31 | HLADR[BB] | CD45[BB] | CD36 | CD105 | CD34[BB] | CD117[BB] | CD33 | CD71 | Diagnosis and subclassification of AML especially focussed on monocytic lineage |
| 32 | HLADR[BB] | CD45[BB] | CD15 | NG2 | CD34[BB] | CD117[BB] | CD7 | CD38 | Diagnosis and subclassification of AML and APL especially focussed on erythroid lineage |
| 33 | HLADR[BB] | CD45[BB] | CD42a plus CD61 | CD203c | CD34[BB] | CD117[BB] | CD123 | CD4 | Diagnosis and subclassification of AML especially focussed on megakaryocytic, basophilic, and plasmacytoid dendritc lineages |
| 34 | HLADR[BB] | CD45[BB] | CD41 | CD25 | CD34[BB] | CD117[BB] | CD42b | CD9 | Characterization of AML/MDS |
| 35 | HLADR[BB] | CD45[BB] | TdT | CD56 | CD34[BB] | CD117[BB] | CD22 | CD19 | Characterization of AML/MDS |

[BB]= Backbone markers; This multi-tube set of antibody combinations is not only useful for AML, MDS and MPD detection, but also for mastocytosis, PNH, ICUS. The tubes can also be successfully applied for disease staging and monitoring.

Schreder M, Seynaeve C, Spacek M, de Tute R M, Van Valckenborgh E, Weston-Bell N, Owen R G, San Miguel J F, Sonneveld P, Johnsen H E; European Myeloma Network. Report of the European Myeloma Network on multiparametric flow cytometry in multiple myeloma and related disorders. Haematologica. 2008; 93:431-8.

5.—Rawstron A C, Villamor N, Ritgen M, Böttcher S, Ghia P, Zehnder J L, Lozanski G, Colomer D, Moreno C, Geuna M, Evans P A, Natkunam Y, Coutre S E, Avery E D, Rassenti L Z, Kipps T J, Caligaris-Cappio F, Kneba M, Byrd J C, Hallek M J, Montserrat E, Hillmen P. International standardized approach for flow cytometric residual disease monitoring in chronic lymphocytic leukaemia. Leukemia. 2007; 21:956-64.

6.—Matutes E, Owusu-Ankomah K, Morilla R, Garcia Marco J, Houlihan A, Que T H, Catovsky D. The immunological profile of B-cell disorders and proposal of a scoring system for the diagnosis of CLL. Leukemia. 1994; 8:1640-5.

The invention claimed is:

1. A reagent composition for flow cytometric immunophenotyping and characterization of lymphoid cell subpopulations, wherein the reagent composition consists essentially of fluorochrome-conjugated antibodies directed against the following combination of cell surface and cytoplasmic markers:

CD45, CD138, CD38, CD56, β2 microglobulin (β2micro), CD19, cytoplasmic IgG kappa chain (CyIgκ), and cytoplasmic IgG lambda chain (CyIgλ), wherein the antibody against CD45, the antibody against CD138, the antibody against CD38, the antibody against CD56, the antibody against β2micro, the antibody against CD19, the antibody against CyIgκ, and the antibody against CyIgλ are each conjugated to a fluorochrome that has a different fluorescence emission from the other fluorochromes.

2. A set of at least two reagent compositions, said set the reagent composition according to claim 1, and at least one further reagent composition comprising fluorochrome-conjugated antibodies directed against one of the following combinations of markers:

(i) CD20, CD45, CD23, CD10, CD79b, CD19, CD200, and CD43, wherein the antibody against CD20, the antibody against CD45, the antibody against CD23, the antibody against CD10, the antibody against CD79b, the antibody against CD19, the antibody against CD200, and the antibody against CD43 are each conjugated to a fluorochrome that has a different fluorescence emission from the other fluorochromes;

(ii) CD20, CD45, CD31, leukocyte-associated immunoglobulin-like receptor 1 (LAIR1), CD11c, CD19, IgM, and CD81, wherein the antibody against CD20, the antibody against CD45, the antibody against CD31, the antibody against leukocyte-associated immunoglobulin-like receptor 1 (LAIR1), the antibody against CD11c, the antibody against CD19, the antibody against IgM, and the antibody against CD81 are each conjugated to a fluorochrome that has a different fluorescence emission from the other fluorochromes;

(iii) CD20, CD45, CD103, CD95, CD22, CD19, CXCR5, and CD49d, wherein the antibody against CD20, the antibody against CD45, the antibody against CD103, the antibody against CD95, the antibody against CD22, the antibody against CD19, the antibody against CXCR5, and the antibody against CD49d are each conjugated to a fluorochrome that has a different fluorescence emission from the other fluorochromes;

(iv) CD20, CD45, CD62L, CD39, human leukocyte antigen-DR (HLADR), CD19, CD27, and CD31, wherein the antibody against CD20, the antibody against CD45, the antibody against CD62L, the antibody against CD39, the antibody against human leukocyte antigen-DR (HLADR), the antibody against CD19, the antibody against CD27, and the antibody against CD31 are each conjugated to a fluorochrome that has a different fluorescence emission from the other fluorochromes;

(v) CD4, CD45, CD7, CD26, CD3, CD2, CD28, and CD8, wherein the antibody against CD4, the antibody against CD45, the antibody against CD7, the antibody against CD26, the antibody against CD3, the antibody against CD2, the antibody against CD28, and the antibody against CD8 are each conjugated to a fluorochrome that has a different fluorescence emission from the other fluorochromes;

(vi) CD4, CD45, CD27, CCR7, CD3, CD45RO, CD45RA, and CD8, wherein the antibody against CD4, the antibody against CD45, the antibody against CD27, the antibody against CCR7, the antibody against CD3, the antibody against CD45RO, the antibody against CD45RA, and the antibody against CD8 are each conjugated to a fluorochrome that has a different fluorescence emission from the other fluorochromes;

(vii) CD4, CD45, CD5, CD25, CD3, HLADR, T cell leukemia/lymphoma 1 (cyTCL1), and CD8, wherein the antibody against CD4, the antibody against CD45, the antibody against CD5, the antibody against CD25, the antibody against CD3, the antibody against HLADR, the antibody against T cell leukemia/lymphoma 1 (cyTCL1), and the antibody against CD8 are each conjugated to a fluorochrome that has a different fluorescence emission from the other fluorochromes;

(viii) CD4, CD45, CD57, CD30, CD3, CD11c, and CD8, wherein the antibody against CD4, the antibody against CD45, the antibody against CD57, the antibody against CD30, the antibody against CD3, the antibody against CD11c, and the antibody against CD8 are each conjugated to a fluorochrome that has a different fluorescence emission from the other fluorochromes;

(ix) CD4, CD45, cyPerforin, cyGranzyme, CD3, CD16, CD94, and CD8, wherein the antibody against CD4, the antibody against CD45, the antibody against cyPerforin, cyGranzyme, the antibody against CD3, the antibody against CD16, the antibody against CD94, and the antibody against CD8 are each conjugated to a fluorochrome that has a different fluorescence emission from the other fluorochromes;

(x) CD4, CD45, CD279, CD3, and CD8, wherein the antibody against CD4, the antibody against CD45, the antibody against CD279, the antibody against CD3, and the antibody against CD8 are each conjugated to a fluorochrome that has a different fluorescence emission from the other fluorochromes;

(xi) CD2, CD45, CD7, CD26, CD3, CD56, CD5, and CD19, wherein the antibody against CD2, the antibody against CD45, the antibody against CD7, the antibody against CD26, the antibody against CD3, the antibody against CD56, the antibody against CD5, and the antibody against CD19 are each conjugated to a fluorochrome that has a different fluorescence emission from the other fluorochromes;

(xii) CD16, CD45, CD57, CD25, CD3, CD56, CD11c, and CD19, wherein the antibody against CD16, the antibody against CD45, the antibody against CD57, the antibody against CD25, the antibody against CD3, the antibody against CD56, the antibody against CD11c, and the antibody against CD19 are each conjugated to a fluorochrome that has a different fluorescence emission from the other fluorochromes;

(xiii) HLADR, CD45, cyPerforin, cyGranzyme, CD3, CD56, CD94, and CD19, wherein the antibody against HLADR, the antibody against CD45, the antibody against cyPerforin, the antibody against cyGranzyme, the antibody against CD3, the antibody against CD56, the antibody against CD94, and the antibody against CD19 are each conjugated to a fluorochrome that has a different fluorescence emission from the other fluorochromes; or (xiv) CD45, CD138, CD38, CD28, CD27, CD19, CD117, and CD81, wherein the antibody against CD45, the antibody against CD138, the antibody against CD38, the antibody against CD28, the antibody against CD27, the antibody against CD19, the antibody against CD117, and the antibody against CD81 are each conjugated to a fluorochrome that has a different fluorescence emission from the other fluorochromes.

3. The reagent composition or set of reagent compositions according to claim 1 or 2, wherein each reagent composition comprises antibodies conjugated to pacific blue (PacB) or Horizon V450, pacific orange (PacO) or aminomethylcoumarin (AMCA), fluorescein isothiocyanate (FITC) or Alexa488, phycoerythrin (PE), peridinin chlorophyll protein (PerCP)-cyanine 5.5 (Cy5.5), PerCP or PE-TexasRed, PE-cyanine 7(Cy7), allophycocyanin (APC) or Alexa647, and APC-H7, APC-Cy7, Alexa680 or Alexa700.

4. The set of reagent compositions according to claim 3, comprising at least one reagent composition comprising fluorochrome-conjugated antibodies directed against the following combinations of markers CD45, CD138, CD38, CD56, β2micro, CD19, CyIgκ, and CyIgλ, wherein the antibody against CD45, the antibody against CD138, the antibody against CD38, the antibody against CD56, the antibody against β2micro, the antibody against CD19, the antibody against CyIgκ, and the antibody against CyIgλ are each conjugated to a fluorochrome that has a different fluorescence emission from the other fluorochromes, together with at least one reagent composition comprising fluorochrome-conjugated antibodies directed against the combination of markers selected from the group consisting of:

(i) CD20, CD4, CD45, Igλ, CD8, Igκ, CD56, CD5, CD19, TCRγδ, CD3, and CD38, wherein the antibodies against CD20 and CD4 are both conjugated to the same fluorochrome, the antibodies against Igλ and CD8 are both conjugated to the same fluorochrome, the antibodies against CD56 and Igκ are both conjugated to the same fluorochrome, and the antibodies against CD19 and TCRγδ are both conjugated to the same fluorochrome, and wherein the antibody against CD20, the antibody against CD45, the antibody against Igλ, the antibody against Igκ, the antibody against CD5, the antibody against CD19, the antibody against CD3, and the antibody against CD38 are each conjugated to a fluorochrome that has a different fluorescence emission from the other fluorochromes;

(ii) CD20, CD45, CD23, CD10, CD79b, CD19, CD200, and CD43, wherein the antibody against CD20, the antibody against CD45, the antibody against CD23, the antibody against CD10, the antibody against CD79b, the antibody against CD19, the antibody against CD200, and the antibody against CD43 are each conjugated to a fluorochrome that has a different fluorescence emission from the other fluorochromes;

(iii) CD20, CD45, CD31, LAIR1, CD11c, CD19, IgM, and CD81, wherein the antibody against CD20, the antibody against CD45, the antibody against CD31, the antibody against leukocyte-associated immunoglobulin-like receptor 1 (LAIR1), the antibody against CD11c, the antibody against CD19, the antibody against IgM, and the antibody against CD81 are each conjugated to a fluorochrome that has a different fluorescence emission from the other fluorochromes;

(iv) CD20, CD45, CD103, CD95, CD22, CD19, CXCR5, and CD49d, wherein the antibody against CD20, the antibody against CD45, the antibody against CD103, the antibody against CD95, the antibody against CD22, the antibody against CD19, the antibody against CXCR5, and the antibody against CD49d are each conjugated to a fluorochrome that has a different fluorescence emission from the other fluorochromes;

(v) CD20, CD45, CD62L, CD39, HLADR, CD19, CD27, and CD31, wherein the antibody against CD20, the antibody against CD45, the antibody against CD62L, the antibody against CD39, the antibody against human leukocyte antigen-DR (HLADR), the antibody against CD19, the antibody against CD27, and the antibody against CD31 are each conjugated to a fluorochrome that has a different fluorescence emission from the other fluorochromes;

(vi) CD4, CD45, CD7, CD26, CD3, CD2, CD28, and CD8, wherein the antibody against CD4, the antibody against CD45, the antibody against CD7, the antibody against CD26, the antibody against CD3, the antibody against CD2, the antibody against CD28, and the antibody against CD8 are each conjugated to a fluorochrome that has a different fluorescence emission from the other fluorochromes;

(vii) CD4, CD45, CD27, CCR7, CD3, CD45RO, CD45RA, and CD8, wherein the antibody against CD4, the antibody against CD45, the antibody against CD27, the antibody against CCR7, the antibody against CD3, the antibody against CD45RO, the antibody against CD45RA, and the antibody against CD8 are each conjugated to a fluorochrome that has a different fluorescence emission from the other fluorochromes;

(viii) CD4, CD45, CD5, CD25, CD3, HLADR, cyTCL1, and CD8, wherein the antibody against CD4, the antibody against CD45, the antibody against CD5, the antibody against CD25, the antibody against CD3, the antibody against HLADR, the antibody against cyTCL1, and the antibody against CD8 are each conjugated to a fluorochrome that has a different fluorescence emission from the other fluorochromes;

(ix) CD4, CD45, CD57, CD30, CD3, CD11c, and CD8, wherein the antibody against CD4, the antibody against CD45, the antibody against CD57, the antibody against CD30, the antibody against CD3, the antibody against CD11c, and the antibody against CD8 are each conjugated to a fluorochrome that has a different fluorescence emission from the other fluorochromes;

(x) CD4, CD45, cyPerforin, cyGranzyme, CD3, CD16, CD94, and CD8, wherein the antibody against CD4, the antibody against CD45, the antibody against cyPerforin, cyGranzyme, the antibody against CD3, the antibody against CD16, the antibody against CD94, and the antibody against CD8 are each conjugated to a fluorochrome that has a different fluorescence emission from the other fluorochromes;

(xi) CD4, CD45, CD279, CD3, and CD8, wherein the antibody against CD4, the antibody against CD45, the antibody against CD279, the antibody against CD3, and the antibody against CD8 are each conjugated to a fluorochrome that has a different fluorescence emission from the other fluorochromes;

(xii) CD2, CD45, CD7, CD26, CD3, CD56, CD5, and CD19, wherein the antibody against CD2, the antibody against CD45, the antibody against CD7, the antibody against CD26, the antibody against CD3, the antibody against CD56, the antibody against CD5, and the antibody against CD19 are each conjugated to a fluorochrome that has a different fluorescence emission from the other fluorochromes;

(xiii) CD16, CD45, CD57, CD25, CD3, CD56, CD11c, and CD19, wherein the antibody against CD16, the antibody against CD45, the antibody against CD57, the antibody against CD25, the antibody against CD3, the antibody against CD56, the antibody against CD11c, and the antibody against CD19 are each conjugated to a fluorochrome that has a different fluorescence emission from the other fluorochromes;

(xiv) HLADR, CD45, cyPerforin, cyGranzyme, CD3, CD56, CD94, and CD19, wherein the antibody against HLADR, the antibody against CD45, the antibody against cyPerforin, the antibody against cyGranzyme, the antibody against CD3, the antibody against CD56, the antibody against CD94, and the antibody against CD19 are each conjugated to a fluorochrome that has a different fluorescence emission from the other fluorochromes;

(xv) CD45, CD138, CD38, CD56, β2micro, CD19, cyIgκ, and cyIgλ, wherein the antibody against CD45, wherein the antibody against CD138, wherein the antibody against CD38, wherein the antibody against CD56, wherein the antibody against β2micro, wherein the antibody against CD19, wherein the antibody against cyIgκ, and wherein the antibody against cyIgλ are each conjugated to a fluorochrome that has a different fluorescence emission from the other fluorochromes; and (xvi) CD45, CD138, CD38, CD28, CD27, CD19, CD117, and CD81, wherein the antibody against CD45, the antibody against CD138, the antibody against CD38, the antibody against CD28, the antibody against CD27, the antibody against CD19, the antibody against CD117, and the antibody against CD81 are each conjugated to a fluorochrome that has a different fluorescence emission from the other fluorochromes.

5. A diagnostic kit for flow cytometric immunophenotyping of lymphoid cell subpopulations comprising the set of at least two reagent compositions according to claim 2, optionally together with instructions for use, buffer, and/or control samples.

6. The diagnostic kit according to claim 5 for the identification and characterization of mature lymphoid cells, comprising the set of reagent compositions recited in claim 2 under (i) through (v); (vi) through (x); (xi) through (xiii); and/or (xiv).

7. A method for flow cytometric immunophenotyping and characterization of lymphoid cell subpopulations, comprising the steps of
(a) providing a biological sample comprising lymphoid cells;
(b) contacting a first aliquot of said sample with a first reagent composition of the set according to claim 2 and contacting at least a second aliquot of said sample with a further reagent composition of said set;
(c) analyzing lymphoid cells in said aliquots in a flow cytometer; and
(d) storing and evaluating the flow cytometric data obtained to characterize the lymphoid cells for the presence of normal and aberrant subpopulations.

8. The method according to claim 7, wherein said sample is peripheral blood, bone marrow, tissue sample, or a body fluid.

9. The method according to claim 7, wherein step (c) comprises the use of software for data integration and multidimensional analysis of flow cytometry files.

10. The method according to claim 9, wherein the software is INFINICYT™.

* * * * *